US010092456B2

(12) United States Patent
Hashimoto et al.

(10) Patent No.: US 10,092,456 B2
(45) Date of Patent: Oct. 9, 2018

(54) DISPOSABLE DIAPER

(71) Applicant: UNICHARM CORPORATION, Ehime (JP)

(72) Inventors: Tatsuya Hashimoto, Kagawa (JP); Norihiro Tokita, Kagawa (JP); Hiroki Goda, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 314 days.

(21) Appl. No.: 14/762,455

(22) PCT Filed: Dec. 26, 2014

(86) PCT No.: PCT/JP2014/084610
§ 371 (c)(1),
(2) Date: Jul. 21, 2015

(87) PCT Pub. No.: WO2016/103482
PCT Pub. Date: Jun. 30, 2016

(65) Prior Publication Data
US 2017/0135867 A1 May 18, 2017

(51) Int. Cl.
A61F 13/15 (2006.01)
A61F 13/49 (2006.01)
(Continued)

(52) U.S. Cl.
CPC .... A61F 13/49001 (2013.01); A61F 13/4902 (2013.01); A61F 13/495 (2013.01);
(Continued)

(58) Field of Classification Search
CPC .... A61F 13/5515; A61F 13/53; A61F 13/534; A61F 13/49001; A61F 13/49017;
(Continued)

(56) References Cited

U.S. PATENT DOCUMENTS 4,636,207 A 1/1987 Buell
2002/0065498 A1* 5/2002 Ohashi .............. A61F 13/4756
604/379
(Continued)

FOREIGN PATENT DOCUMENTS

CN 101087573 A 12/2007
CN 102149358 A 8/2011
(Continued)

OTHER PUBLICATIONS

Extended European Search Report in EP application No. 14877551.3, dated May 3, 2016.
(Continued)

Primary Examiner — Jacqueline Stephens
(74) Attorney, Agent, or Firm — Hauptman Ham, LLP

(57) ABSTRACT

A disposable diaper, having a longitudinal direction and a lateral direction, an absorbent main body having an absorbent body, a back waist part located on one end of the absorbent main body, and an abdominal waist part located on another end of the absorbent body, the absorbent body having side parts in the lateral direction provided with a pair of embossed lines formed by embossing from a skin side of the absorbent body, and the embossed lines each including a protrusion point, protruding inward in the lateral direction, located in a center of the disposable diaper in the longitudinal direction in a midsection of the disposable diaper or on a back waist part side with respect to the center, and a back line, linear or curved outward, extending outward in the lateral direction from the protrusion point, as a starting point, toward the back waist part in the longitudinal direction.

12 Claims, 7 Drawing Sheets

(51) Int. Cl.
*A61F 13/495* (2006.01)
*A61F 13/535* (2006.01)
*A61F 13/534* (2006.01)
*A61F 13/551* (2006.01)
*A61F 13/53* (2006.01)

(52) U.S. Cl.
CPC ...... *A61F 13/49017* (2013.01); *A61F 13/535* (2013.01); *A61F 13/534* (2013.01); *A61F 13/5515* (2013.01); *A61F 2013/49025* (2013.01); *A61F 2013/530007* (2013.01); *A61F 2013/53454* (2013.01)

(58) Field of Classification Search
CPC ................ A61F 13/4902; A61F 13/535; A61F 2013/530007; A61F 2013/49025
USPC .......................... 604/378, 379, 380, 385.101
See application file for complete search history.

(56) References Cited

U.S. PATENT DOCUMENTS

| | | | |
|---|---|---|---|
| 2007/0244455 | A1 | 10/2007 | Hansson et al. |
| 2012/0095425 | A1* | 4/2012 | Nishitani .......... A61F 13/47218 604/380 |

FOREIGN PATENT DOCUMENTS

| | | |
|---|---|---|
| CN | 103260570 A | 8/2013 |
| JP | 2011-36502 A | 2/2001 |
| JP | 2001-258935 A | 9/2001 |
| JP | 2001-340383 A | 12/2001 |
| JP | 2007-117727 A | 5/2007 |
| JP | 2008-73449 A | 4/2008 |
| JP | 2008-125917 A | 6/2008 |
| JP | 2008-525100 A | 7/2008 |
| JP | 2009-119154 A | 6/2009 |
| JP | 2010-51654 A | 3/2010 |
| JP | 2012-143535 A | 8/2012 |
| JP | 2014-188253 A | 10/2014 |
| TW | 201404378 A | 2/2014 |
| TW | 201410219 A | 3/2014 |
| WO | 2004/103238 A1 | 12/2004 |
| WO | 2010/030007 A1 | 3/2010 |
| WO | 2010/064580 A1 | 6/2010 |
| WO | 2014/204015 A1 | 12/2014 |

OTHER PUBLICATIONS

Office Action in PH Application No. 1/2015/501574 dated Nov. 24, 2016.
Office Action in TW Application No. 104118776, dated Dec. 5, 2016.
Written Opinion dated Mar. 31, 2015 in International Application No. PCT/JP2014/084610.
Office Action in CN Application No. 201480006825.2, dated Sep. 7, 2016.
Translation of International Preliminary Report on Patentability and Written Opinion of the ISA in PCT/JP2014/084610 dated Jul. 6, 2017. 8pp.
Office Action in JP Application No. 2015-106352, dated Aug. 14, 2018, 2pp.

\* cited by examiner

OUTSIDE CURVATURE

INSIDE CURVATURE

DISPOSABLE DIAPER

RELATED APPLICATIONS

The present application is a National Phase of International Application Number PCT/JP2014/084610, filed Dec. 26, 2014.

TECHNICAL FIELD

The present invention relates to a disposable diaper.

BACKGROUND ART

Conventionally, disposable diapers are widely used for infants and the like as target users. These disposable diapers each include: an absorbent main body having an absorbent body that absorbs excreta; a back waist part located on one end side of the absorbent main body; and an abdominal waist part located on the other end side of the absorbent main body.

Then, among these disposable diapers, some diapers are provided with a pair of embossed lines formed by embossing in both side parts in the lateral direction of the absorbent body. With such embossed lines being provided, a part of an absorbent body corresponding to a crotch can be formed in a simple cup shape (which is formed such that the absorbent body is folded along the embossed lines and absorbent-body outer-side parts, located on the outer side with respect to the embossed lines, standup), thereby being able to create a space to contain excreta.

CITATION LIST

Patent Literature

[PTL 1] Japanese translation of PCT International application No. 2008-525100

SUMMARY OF INVENTION

Technical Problem

However, in such a disposable diaper according to a conventional example, since the embossed lines are provided such that the absorbent body is formed in a cup shape at a crotch, the absorbent body on the back side with respect to the crotch, that is, a part of the absorbent body corresponding to buttocks, is affected by the embossed lines, and thereby the absorbent-body outer-side parts stand up also at buttocks (slip inward), which causes a problem that buttocks cannot be widely covered with the absorbent body.

The present invention has been made in view of the above described problem, and an objective thereof is to provide a disposable diaper that is capable of extensively covering buttocks with an absorbent body, while maintaining formation of a part of the absorbent body corresponding to a crotch in a simple cup shape.

Solution to Problem

In order to achieve an object described above, an aspect of the invention is a disposable diaper having a longitudinal direction and a lateral direction intersecting the longitudinal direction, the disposable diaper including:

an absorbent main body including an absorbent body that absorbs excreta;

a back waist part located on one end side of the absorbent main body; and an abdominal waist part located on an other end side of the absorbent main body, the absorbent body having both side parts, in the lateral direction, provided with a pair of embossed lines that is formed by embossing from a skin side of the absorbent body, the embossed lines each including a protrusion point, protruding inward in the lateral direction, located in a center of the disposable diaper or on a back-waist-part side with respect to said center, in the longitudinal direction, in a midsection of the disposable diaper, and a back line extending outward in the lateral direction from the protrusion point, serving as a starting point, toward the back waist part in the longitudinal direction, the back line being a straight line or an outwardly curved line.

Other features of the present invention will be made clear through the present specification with reference to the accompanying drawings.

Advantageous Effects of Invention

According to the present invention, it is possible to provide a disposable diaper that can widely cover buttocks with an absorbent body, while maintaining formation of a part of the absorbent body corresponding to a crotch in a simple cup form.

DESCRIPTION OF EMBODIMENTS

Figure 1:
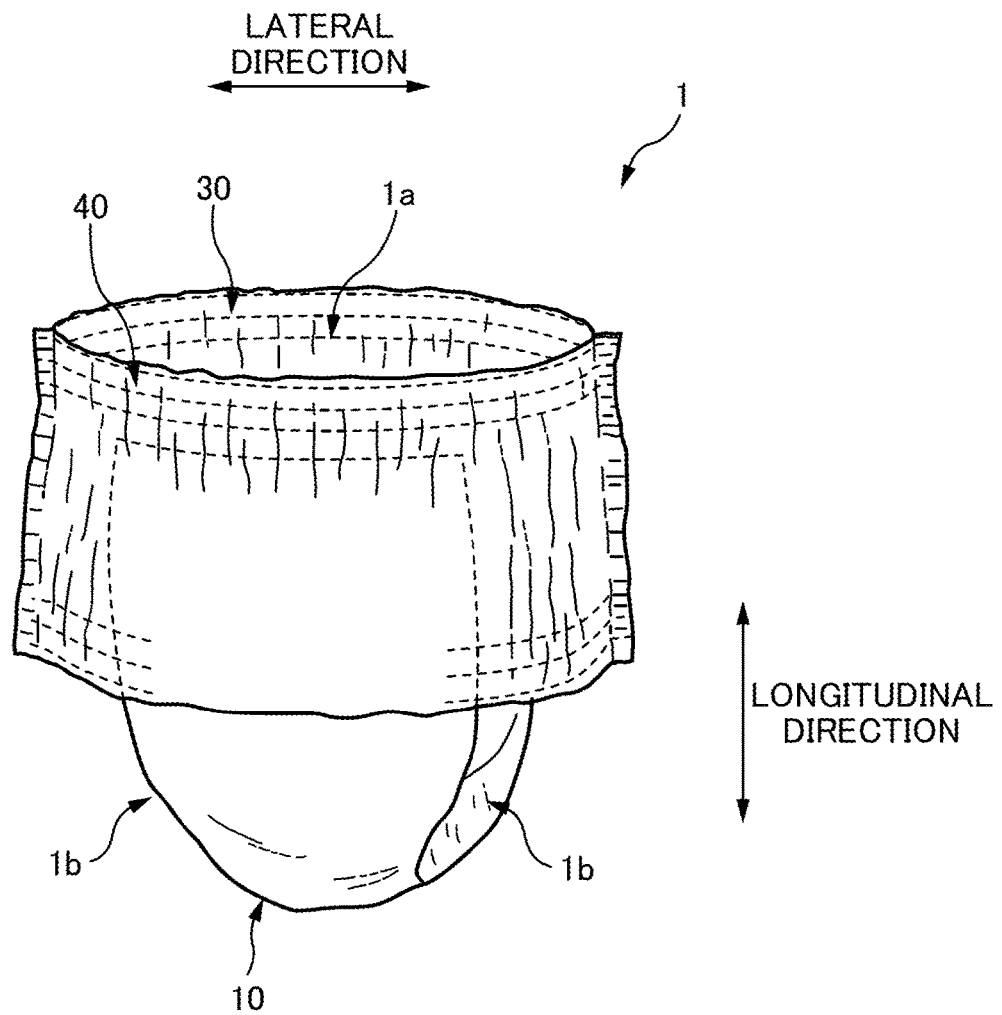
FIG. 1 is a perspective image view illustrating a disposable diaper according to a present embodiment.

At least the following matters will become clear from the description of the present specification with reference to the accompanying diagrammatic drawings.

A disposable diaper having a longitudinal direction and a lateral direction intersecting the longitudinal direction, the disposable diaper including: an absorbent main body including an absorbent body that absorbs excreta; a back waist part located on one end side of the absorbent main body; and an abdominal waist part located on an other end side of the absorbent main body, the absorbent body having both side parts, in the lateral direction, provided with a pair of embossed lines that is formed by embossing from a skin side of the absorbent body, the embossed lines each including a protrusion point, protruding inward in the lateral direction, located in a center of the disposable diaper or on a back-waist-part side with respect to said center, in the longitudinal direction, in a midsection of the disposable diaper, and a back line extending outward in the lateral direction from the protrusion point, serving as a starting point, toward the back waist part in the longitudinal direction, the back line being a straight line or an outwardly curved line.

According to such a disposable diaper, buttocks can be widely covered with the absorbent body, while formation of apart of the absorbent body corresponding to a crotch is being maintained in a simple cup shape.

In such a disposable diaper, it is desirable that a notch is provided at a location corresponding to a position of the protrusion point in the longitudinal direction, in a side edge in the lateral direction of the absorbent body.

According to such a disposable diaper, a space to contain excreta can be formed more appropriately. Further, a part of the absorbent body corresponding to a crotch can be formed in a simple cup shape more appropriately.

In such a disposable diaper, it is desirable that a fold line is formed along the lateral direction at a location corresponding to a position of the protrusion point in the longitudinal direction.

According to such a disposable diaper, a space to contain excreta can be formed more appropriately.

In such a disposable diaper, it is desirable that elastic members along the longitudinal direction are provided to the absorbent main body.

According to such a disposable diaper, a space to contain excreta can be formed further appropriately.

In such a disposable diaper, it is desirable that the elastic members are rubber threads provided to leg side gathers, and the rubber threads are located on an outer side in the lateral direction with respect to the protrusion point.

According to such a disposable diaper, apart of an absorbent body corresponding to a crotch can be formed in a simple cup shape more appropriately.

In such a disposable diaper, it is desirable that the back line is the outwardly curved line.

According to such a disposable diaper, buttocks can be further widely covered with the absorbent body, and further, the back line can be made along the shape of buttocks. Further, the absorbent body can be more appropriately restrained from being inserted into buttocks, thereby being able to more reliably restrain degradation of feeling to the touch.

In such a disposable diaper, it is desirable that the absorbent body contains pulp and absorbent polymer, the absorbent body includes first regions, and second regions in which a ratio of absorbent polymer divided by pulp is smaller than the ratio in the first regions, and the embossed lines are provided in the second regions.

According to such a disposable diaper, a part of the absorbent body corresponding to a crotch can be formed in a simple cup shape more appropriately.

In such a disposable diaper, it is desirable that raised parts are provided to both sides of the embossed lines in the lateral direction.

According to such a disposable diaper, it can be avoided that the absorbent body is excessively folded along the embossed lines.

In such a disposable diaper, it is desirable that an ending point of the back line reaches a side edge in the lateral direction of the absorbent body.

According to such a disposable diaper, buttocks can be extensively covered with the absorbent body.

In such a disposable diaper, it is desirable that a side edge of an overlap part overlapping with the back waist part of the absorbent body and a side edge of a non-overlap part not overlapping with the back waist part of the absorbent body are provided as the side edge, and the ending point reaches the side edge of the non-overlap part.

According to such a disposable diaper, buttocks can be more widely covered with the absorbent body.

In such a disposable diaper, it is desirable that the ending point is located in an intermediate part between a lower end, of the back waist part, on a side closer to the said center and the protrusion point, in the longitudinal direction.

According to such a disposable diaper, a cup shape can be formed more appropriately, while buttocks are being more extensively covered with the absorbent body.

In such a disposable diaper, it is desirable that the embossed lines each include a second protrusion point, different from the protrusion point, located on an abdominal-waist-part side with respect to the said center, and an abdominal line extending outward in the lateral direction from the second protrusion point, serving as a starting point, toward the abdominal waist part in the longitudinal direction, an ending point of the abdominal line reaches a side edge in the lateral direction of the absorbent body, a side edge of an overlap part overlapping with the abdominal waist part of the absorbent body and a side edge of a non-overlap part not overlapping with the abdominal waist part of the absorbent body are provided as the side edge, and the ending point reaches the side edge of the overlap part.

According to such a disposable diaper, a part of the absorbent body corresponding to an abdomen can be formed in a simple cup shape.

In such a disposable diaper, it is desirable that the embossed lines each include a second protrusion point, different from the protrusion point, located on an abdominal-waist-part side with respect to the said center, and an abdominal line extending outward in the lateral direction from the second protrusion point, serving as a starting point, toward the abdominal waist part in the longitudinal direction, and the abdominal line is an inwardly curved line.

According to such a disposable diaper, the absorbent body can be formed in such a shape as to allow freedom of legs movement.

In such a disposable diaper, it is desirable that the embossed lines each include a third protrusion point between the protrusion point and the second protrusion point, and notches are respectively provided at locations corresponding to positions of the second protrusion point and the third protrusion point in the longitudinal direction, in a side edge in the lateral direction of the absorbent body.

According to such a disposable diaper, a space to contain an excretory portion can be more appropriately formed throughout the entire crotch.

Disposal Diaper According to Present Embodiment

Figure 2:
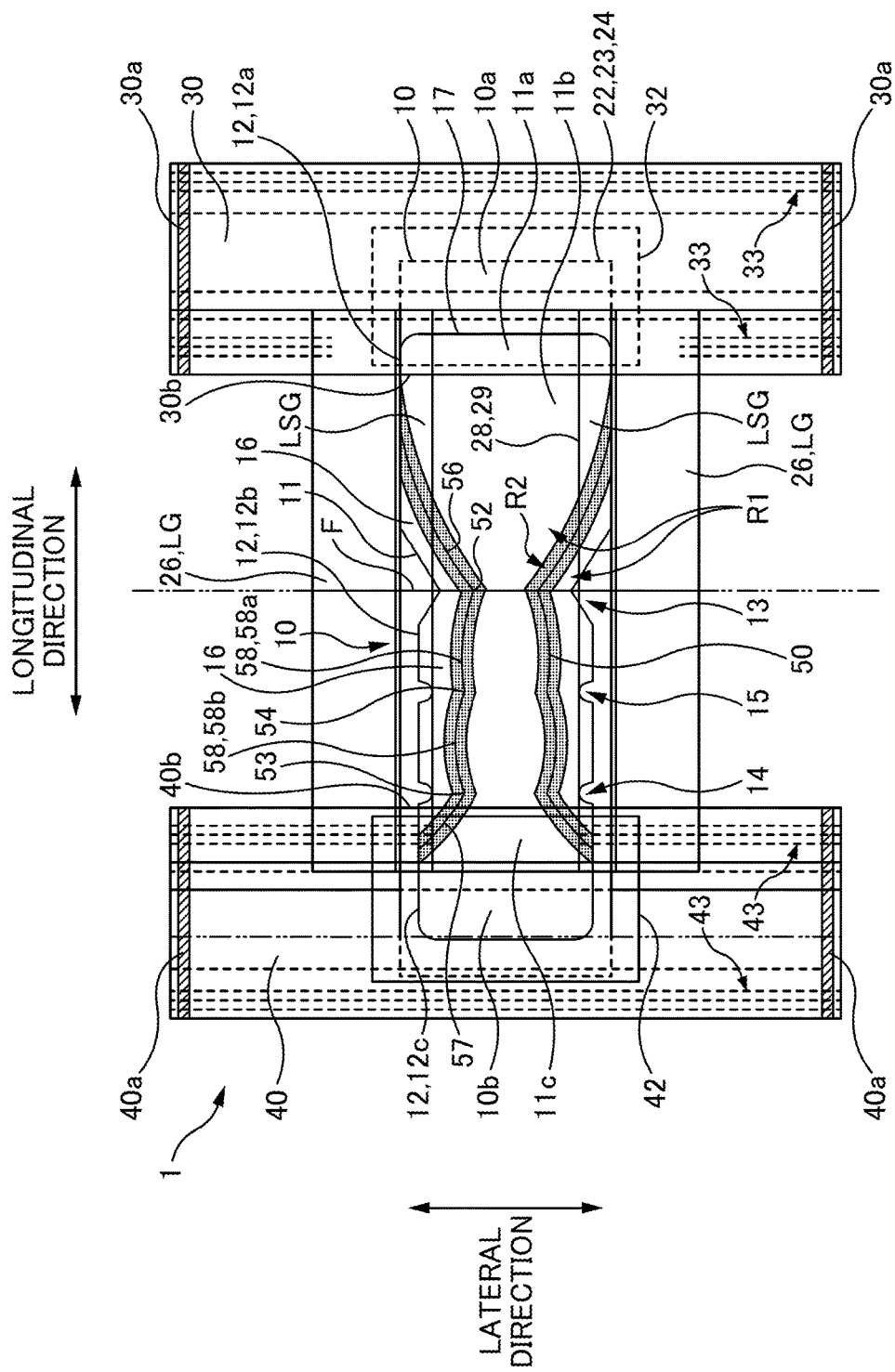
FIG. 2 is a plan view illustrating the diaper 1 in its unfolded state.
Figure 3:
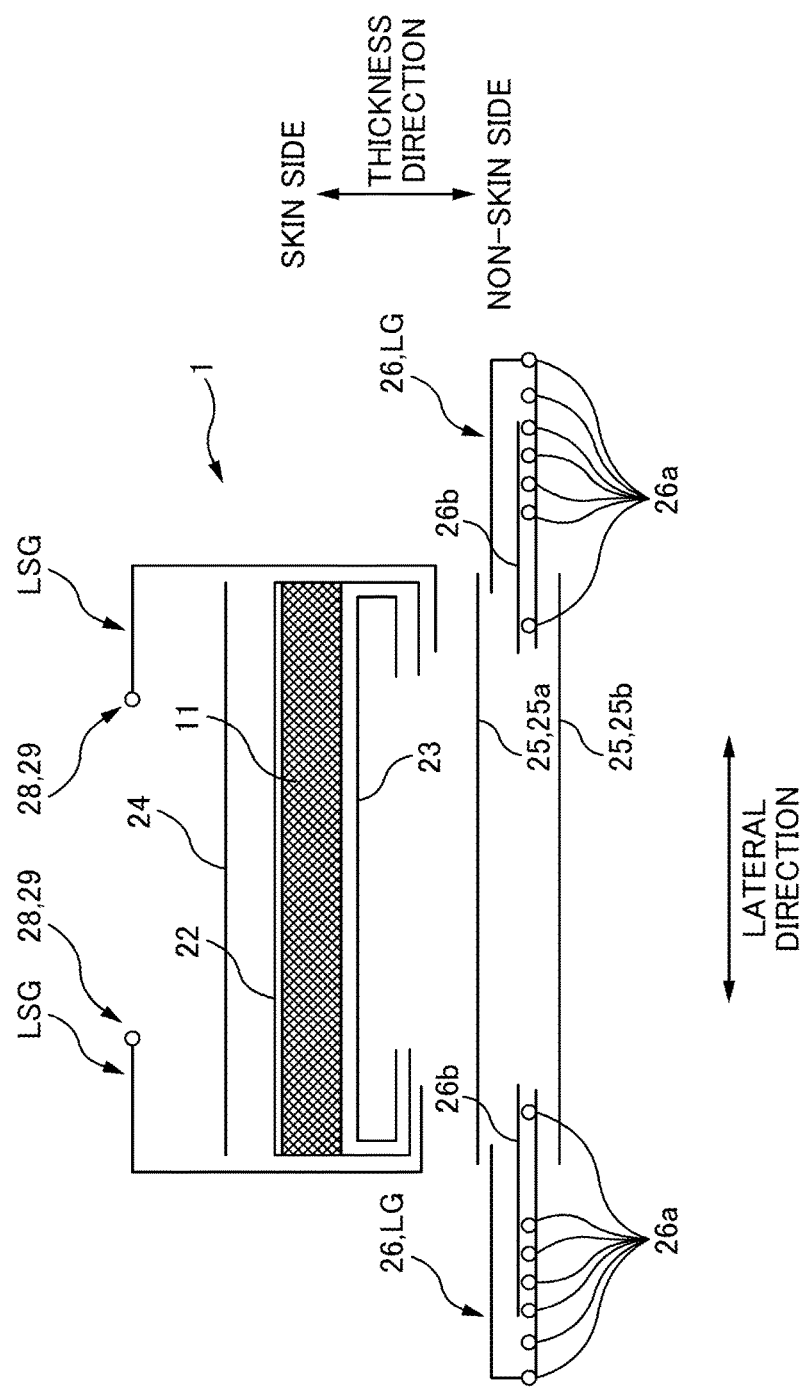
FIG. 3 is a schematic cross-sectional view illustrating the diaper 1 in its unfolded state.

FIG. 1 is a perspective image view illustrating a disposable diaper according to a present embodiment (hereinafter, simply referred to as a diaper 1). FIG. 2 is a plan view illustrating the diaper 1 in an unfolded state. FIG. 3 is a schematic cross-sectional view illustrating the diaper 1 in an unfolded state.

Main targets, as wearers, for the disposable diaper according to a present embodiment (hereinafter, also simply referred to as the diaper 1) are infants such as babies.

In the following description, a longitudinal direction, a lateral direction and a thickness direction of the diaper 1 are simply referred to as the "longitudinal direction," the "lateral direction," and the "thickness direction," respectively. Note that, regarding the thickness direction, the side to come in contact with a wearer is referred to as a "skin side," and the side opposite thereto is referred to as a "non-skin side." Further, in the following description, the "lateral direction" is also referred to as the "width direction."

The diaper 1 according to a present embodiment has the longitudinal direction, the lateral direction, and the thickness direction as three directions intersecting (orthogonal to) one another. Further, the diaper 1 is the so-called three-piece type and has three components. That is, the diaper 1 includes: an absorbent main body 10 structured to be provided to a crotch of a wearer and absorbs excreta such as urine, as a first component; a back waist part 30 structured to cover a back side of the wearer, as a second component; and an abdominal waist part 40 structured to cover an abdomen side of the wearer, as a third component.

In the unfolded state in FIG. 2, the back waist part 30 and the abdominal waist part 40 are arranged in parallel to each other with a space therebetween in the longitudinal direction, and the absorbent main body 10 bridges the space therebetween. Then, the back waist part 30 is fixed to one end section 10a of the absorbent main body 10 and the abdominal waist part 40 is fixed to the other end section 10b thereof, and the external appearance thereof is formed in an H-shape in plan view. In other words, the back waist part 30 is located on one end side of the absorbent main body 10, and the abdominal waist part 40 is located on the other end side of the absorbent main body 10.

Then, from this state, the absorbent main body 10 is folded into two at the center of the diaper in the lengthwise direction (i.e., the longitudinal direction) (the center, in the longitudinal direction, between one end and the other end of the unfolded diaper 1) as a folding position (thus, at this folding position, a fold line F is formed along the lateral direction). When the back waist part 30 and the abdominal waist part 40, opposed to each other in this two-folded state, are joined/coupled, these waist parts are formed in an annular shape. That is, the diaper 1 is formed, with both edge parts 30a in the lateral direction of the back waist part 30 and both edge parts 40a in the lateral direction of the abdominal waist part 40 being respectively joined to each other. Thereby, the diaper 1 when worn is structured, in which a waist opening 1a and a pair of leg openings 1b is formed as illustrated in FIG. 1.

The back waist part 30 is a sheet-like member corresponding to a back portion of a wearer. This back waist part 30 is in a rectangular shape in plan view, and arranged such that the lengthwise direction (direction of its long sides) is along the lateral direction. The back waist part 30 is made of nonwoven fabric. Note that, in a present embodiment, an illustration sheet 32 with illustrations (not shown), such as floral pattern, is provided. The back waist part 30 overlaps with the one end section 10a of the absorbent main body 10, and is joined to be fixed thereto.

Further, in the back waist part 30, a plurality of elastic members (specifically, rubber threads, referred to as back rubber threads 33, for convenience' sake), which expand and contract along the lateral direction, are arranged. These back rubber threads 33 are joined and fixed to the nonwoven fabric. This imparts stretchability in the lateral direction to the back waist part 30, thereby providing stretchability to the waist opening 1a of the diaper 1.

The abdominal waist part 40 is a sheet-like member corresponding to an abdomen of a wearer. This abdominal waist part 40 is in a rectangular shape in plan view, and arranged such that the lengthwise direction (direction of its long sides) is along the lateral direction. The abdominal waist part 40 is made of nonwoven fabric. Note that, in a present embodiment, an illustration sheet 42 with illustrations (not shown), such as floral pattern, is provided. The abdominal waist part 40 overlaps with the other end section 10b of the absorbent main body 10, and joined to be fixed thereto.

Further, in the abdominal waist part 40, a plurality of elastic members (specifically, rubber threads, referred to as abdominal rubber threads 43, for convenience' sake), which expand and contract along the lateral direction, are arranged. These abdominal rubber threads 43 are joined and fixed to the nonwoven fabric. This imparts stretchability in the lateral direction to the abdominal waist part 40, thereby providing stretchability to the waist opening 1a of the diaper 1.

<<<Structure of Absorbent Main Body 10>>>

A part of the absorbent main body 10 corresponds to a crotch of a wearer, and is to absorb excreta such as urine. This absorbent main body 10 is, as illustrated in FIG. 2, in a rectangular shape in plan view, and arranged such that the lengthwise direction thereof (direction of its long sides) is along the longitudinal direction.

The absorbent main body 10 includes an absorbent body 11 (hereinafter, also referred to as an absorbent core), an upper core wrap 22, a lower core wrap 23, a top sheet member 24, and a back sheet member 25.

The absorbent body 11 is a member (absorbent core) formed such that liquid absorbent materials are stacked, and is the member capable of absorbing excreta such as urine. The absorbent body 11 includes pulp (pulp fibers) and absorbent polymer(s) (SAP). The absorbent body 11 according to a present embodiment has substantially an hourglass shape in plan view.

The upper core wrap 22 and the lower core wrap 23 are, as illustrated in FIG. 3, liquid permeable sheets (nonwoven fabric) that cover the absorbent body 11 by being sandwiched from the upper side (skin side) and the lower side (non-skin side) in the thickness direction. The upper core wrap 22 and the lower core wrap 23 are, as illustrated in FIG. 2, in a rectangular shape in plan view, have a planar size slightly larger than that of the absorbent body 11, and cover the absorbent body 11 therewith.

The top sheet member 24 is, as illustrated in FIG. 3, a sheet-like liquid permeable nonwoven fabric that covers the absorbent body 11, sandwiched between the upper core wrap 22 and the lower core wrap 23, from the upper side (skin side). This top sheet member 24 is also in a rectangular shape in plan view, and has a planar size slightly larger than that of the absorbent body 11 (planar size substantially similar to those of the upper core wrap 22 and the lower core wrap 23).

The back sheet member 25 is, as illustrated in FIG. 3, a sheet-like member that covers the absorbent body 11, sandwiched between the upper core wrap 22 and the lower core wrap 23, from the lower side (non-skin side). This back sheet member 25 is also in a rectangular shape in plan view, and has a planar size slightly larger than that of the absorbent body 11. The back sheet member 25 according to a present embodiment is a sheet having a two-layer structure made of a liquid-impermeable leak-proof sheet 25a, such as polyethylene, polypropylene, or the like, and an exterior sheet 25b such as nonwoven fabric.

Further, regions located in both side parts in the width direction of the absorbent main body 10, that is, side flaps 26 in a pair are, as illustrated in FIG. 3, respectively provided with leg gathers LG (elastic parts around legs) which expand and contract along the longitudinal direction. The leg gathers LG are made of nonwoven fabric located between the leak-proof sheet 25a and the exterior sheet 25b, and includes: elastic members (specifically, rubber threads, referred to as LG rubber threads 26a, for convenience' sake) that expand and contract along the longitudinal direction; and aside film 26b. Then, the LG rubber threads 26a impart stretchability to the side flaps 26, thereby the leg gathers LG are structured.

Further, a pair of leg side-gathers LSG (solid gathers) is provided, as illustrated in FIG. 2, in the inner side with respect to the leg gathers LG (side flaps 26) in the width direction of the absorbent main body 10. The leg side-gathers LSG are provided on the skin side of the absorbent main body 10, and serve a function of restraining liquid leakage from gaps around legs. The leg side-gathers LSG are made of nonwoven fabric. The leg side-gathers LSG have top parts 28 on inner ends of the leg side-gathers LSG in the width direction of the absorbent main body 10, and the top parts 28 and the nonwoven fabrics on the outer side with respect to the top part 28 are structured to stand up. Further, the top parts 28 of the leg side-gathers LSG are provided with elastic members (specifically, rubber threads, referred to as LSG rubber threads 29, for convenience' sake), which expand and contract along the longitudinal direction.

<Embossed Line 50>

Figure 4:
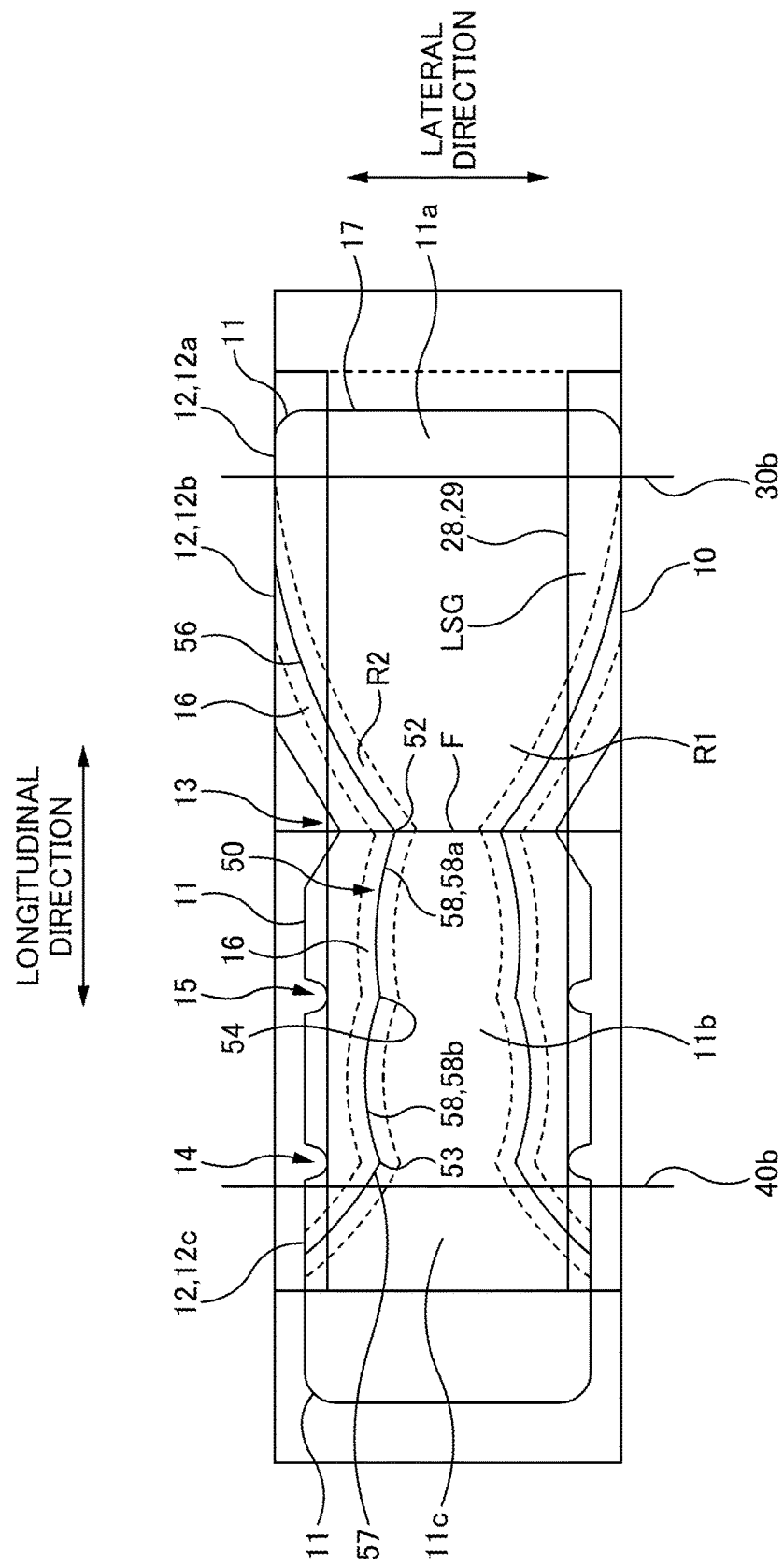
FIG. 4 is an explanatory view to explain forms of embossed lines 50.
Figure 5:
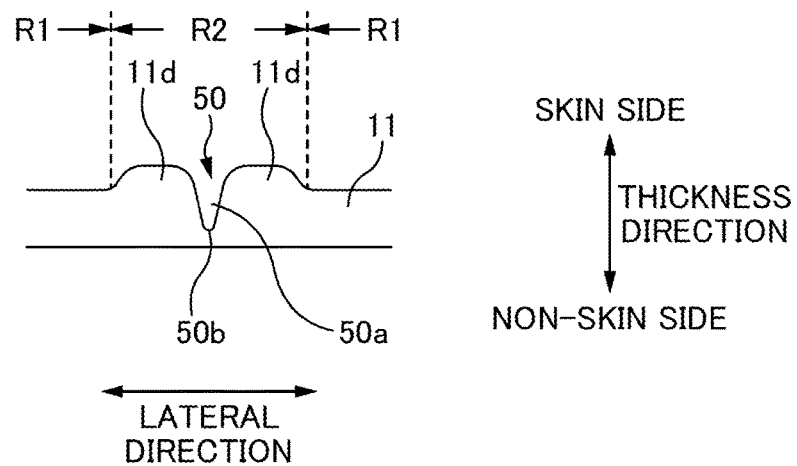
FIG. 5 is an image cross-sectional view illustrating a cross section of the embossed line 50.

A pair of embossed lines 50 formed by embossing is provided to the absorbent body 11 according to a present embodiment. Hereinafter, the embossed lines 50 will be described with reference to FIGS. 4 and 5. FIG. 4 is an explanatory view to explain forms of the embossed lines 50. FIG. 5 is an image cross-sectional view illustrating a cross section of the embossed line 50.

The embossed lines 50 are structured to create a space to contain excreta by forming a part of the absorbent body 11, which corresponds to a crotch, in a cup shape (which is formed by folding the absorbent body 11 along the embossed lines 50) (which will be described later in detail). This pair of the embossed lines 50 is provided in both side parts in the lateral direction of the absorbent body 11. The embossed lines 50 are line-symmetric with respect to a center line in the lateral direction of the absorbent body 11, serving as an axis of symmetry. As such, since both the embossed lines 50 are similar to each other, the embossed line 50 on one side will hereinafter be described.

The embossed line 50 includes a first protrusion point 52 (corresponding to a protrusion point), a second protrusion point 53, a third protrusion point 54, a back line 56, an abdominal line 57, and a center line 58. Note that the first protrusion point 52 is the top point that protrudes inward in the lateral direction. This first protrusion point 52 is located in the center of the diaper 1 in the longitudinal direction (the center in the longitudinal direction between one end and the other end of the diaper 1 in an unfolded state, which is indicated by a two-dot chain line in FIG. 2) or is located on the side of the back waist part 30 with respect to the said center, in a midsection of the diaper 1. In other words, the first protrusion point 52 is arranged in a position corresponding to that on the back side with respect to the center of a crotch (on the side closer to the back waist part 30). Specifically, the first protrusion point 52 is arranged on the said center side with respect to the midpoint between the said center and a lower end 30b, of the back waist part 30, on the side closer to the said center, and is located substantially in the said center in a present embodiment. Thus, the aforementioned fold line F is formed in a position corresponding to the position of the first protrusion point 52 in the longitudinal direction.

Further, the first protrusion point 52 protrudes inward on the inner side in the lateral direction with respect to the aforementioned LSG rubber threads 29. That is, the LSG rubber threads 29 are positioned on the outer side in the lateral direction with respect to the first protrusion point 52.

The back line 56 is a line, which is straight or curved outward (curved outward in a present embodiment), extending outward in the lateral direction from the first protrusion point 52, serving as a starting point, toward the back waist part 30 in the longitudinal direction.

Further, the back line 56 extends toward a side edge 12 in the lateral direction of the absorbent body 11, and an ending point of the back line 56 reaches the side edge 12. More specifically, a side edge of a back overlap part 11a overlapping with the back waist part 30 of the absorbent body 11 (referred to as a back overlap part side edge 12a, for convenience' sake), and a side edge of a non-overlap part 11b not overlapping with the back waist part 30 of the absorbent body 11 (referred to as a non-overlap part side edge 12b, for convenience' sake) exist as the side edge 12, and the ending point reaches the non-overlap part side edge 12b. That is, the ending point of the back line 56 reaches the side edge 12 on the near side (on the said center side), in the longitudinal direction, with respect to the lower end 30b of the back waist part 30. Note that, in a present embodiment, the ending point is located in an intermediate part between the lower end 30b and the first protrusion point 52 in the longitudinal direction.

As such, the back line 56 according to a present embodiment results in a line curved outward from the starting point (first protrusion point 52) to the ending point (non-overlap part side edge 12b).

The second protrusion point 53 is a top point that protrudes inward in the lateral direction, similarly to the first protrusion point 52. This second protrusion point 53 is located on the side of the abdominal waist part 40 with respect to the said center. In other words, the second protrusion point 53 is arranged in a position corresponding to that on the abdominal side with respect to the center of a crotch (on the side closer to the abdominal waist part 40). In a present embodiment, the second protrusion point 53 is located in the vicinity of a lower end 40b, of the abdominal waist part 40, on the side closer to the said center.

Further, the second protrusion point 53 protrudes inward on the inner side in the lateral direction with respect to the aforementioned LSG rubber threads 29, similarly to the first protrusion point 52. That is, the LSG rubber threads 29 are positioned on the outer side in the lateral direction with respect to the second protrusion point 53.

The abdominal line 57 is an inwardly curved line extending outward in the lateral direction from the second protrusion point 53, serving as a starting point, toward the abdominal waist part 40 in the longitudinal direction.

Further, the abdominal line 57 extends toward the side edge 12 in the lateral direction of the absorbent body 11, and the ending point of the abdominal line 57 reaches the side edge 12. More specifically, a side edge of an abdominal overlap part 11c overlapping with the abdominal waist part 40 of the absorbent body 11 (referred to as an abdominal overlap part side edge 12c, for convenience' sake), and the aforementioned non-overlap part side edge 12b not overlapping with the abdominal waist part 40 (or the back waist part 30, either) of the absorbent body 11 exist as the side edge 12, and the ending point reaches the abdominal overlap part side edge 12c. That is, the ending point of the abdominal line 57 reaches the side edge 12 beyond the lower end 40b of the abdominal waist part 40 in the longitudinal direction.

As such, the abdominal line 57 according to a present embodiment is a line curved inward from the starting point (second protrusion point 53) to the ending point (abdominal overlap part side edge 12c).

The third protrusion point 54 is atop point that protrudes inward in the lateral direction, similarly to the first protrusion point 52 and the second protrusion point 53, and is arranged between the first protrusion point 52 and the second protrusion point 53 (substantially in an intermediate part in a present embodiment) in the embossed line 50. This third protrusion point 54 is located on the side of the abdominal waist part 40 with respect to the said center. In other words, the third protrusion point 54 is arranged in a position corresponding to the center of a crotch.

Further, the third protrusion point 54 protrudes inward on the inner side in the lateral direction with respect to the aforementioned LSG rubber threads 29, similarly to the first protrusion point 52 and the second protrusion point 53. That is, the LSG rubber threads 29 are positioned on the outer side in the lateral direction with respect to the third protrusion point 54.

The center line 58 is a line connecting the back line 56 and the abdominal line 57, and includes a first center line 58a and a second center line 58b.

The first center line 58a is a line from the first protrusion point 52 to the third protrusion point 54, and the second center line 58b is a line from the second protrusion point 53 to the third protrusion point 54, and both are outwardly curved lines.

Note that the first protrusion point 52 is positioned on the inner side in the lateral direction with respect to the second protrusion point 53 and the third protrusion point 54. Thus, in the longitudinal direction, the width of the absorbent body 11 is narrowest at the position at which the first protrusion point 52 is located (result in a narrowest width part).

Further, a first notch 13 is provided at a location corresponding to the position of the first protrusion point 52 in the longitudinal direction, in the side edge 12 of the absorbent body 11. Further, a second notch 14 and a third notch 15 are respectively provided at locations corresponding to positions of the second protrusion point 53 and the third protrusion point 54 in the longitudinal direction in the side edge 12. That is, the first notch 13 (second notch 14, third notch 15) is provided at a part of the absorbent body 11 (hereinafter, referred to as an absorbent body outer part 16, for convenience' sake) located on the outer side in the lateral direction with respect to the embossed line 50, and the position in the longitudinal direction of the first notch 13 (second notch 14, third notch 15) substantially coincide with the position in the longitudinal direction of the first protrusion point 52 (second protrusion point 53, third protrusion point 54).

Further, the embossed line 50 is a line formed by embossing from the skin side of the absorbent body 11. Thus, as illustrated in FIG. 5, in the embossed line 50, a large depression 50a is formed on the skin side of the absorbent body 11, resulting in a compressed part 50b formed on the non-skin side with respect to the depression 50a. Note that embossing from the skin side may be carried out for the absorbent core or the absorbent core covered with a core wrap, or over the top sheet member 24.

Further, the absorbent body 11 according to a present embodiment includes: first regions R1 (regions other than dotted parts in FIG. 2); and a second region R2 (the dotted part in FIG. 2) in which the absorbent polymer(s) to pulp ratio (ratio of absorbent polymer(s) divided by pulp) is smaller than the ratio in the first regions R1, and the embossed line 50 is formed in the second region R2. That is, a region in which an absorbent polymer(s) to pulp ratio is smaller than a normal ratio is provided, and the embossed line 50 is to be formed in this region. In other words, as illustrated in FIG. 2, the second region R2 is formed along the embossed line 50.

Further, in a present embodiment, the embossed line 50 is formed in the second region R2 containing less absorbent polymers relative to pulp. Since the second region R2 is less easily compressed due to less absorbent polymers, formation of the embossed line 50 causes parts on both sides of the embossed line 50 in the lateral direction to resist and become slightly raised. That is, raised parts 11d are provided to both sides of the embossed line 50 in the lateral direction.

Availability of Diaper 1 According to Present Embodiment

As described above, the diaper 1 according to a present embodiment has the longitudinal direction and the lateral direction intersecting the longitudinal direction, and includes: the absorbent main body 10 having the absorbent body 11 that absorbs excreta; the back waist part 30 located on one side of the absorbent main body 10; and the abdominal waist part 40 located on the other end of the absorbent main body 10. Further, a pair of embossed lines 50, which is formed by embossing from the skin side of the absorbent body 11, is provided in both side parts in the lateral direction of the absorbent body 11. The embossed lines 50 are to include: the first protrusion point 52 that is located in the center of the diaper 1 or on the back waist part 30 side with respect to the said center, in the longitudinal direction, in the midsection of the diaper 1, and that protrudes inward in the lateral direction; and the back line 56, which is a straight line of an outwardly curved line, extending outward in the lateral direction from the first protrusion point 52, serving as the starting point, toward the back waist part 30 in the longitudinal direction. Thus, it is possible to achieve the diaper 1 capable of widely covering buttocks with the absorbent body 11, while maintaining formation of a part of the absorbent body 11 corresponding to a crotch being in a simple cup shape.

Conventionally, diapers 1 have been widely used each include: an absorbent main body 10 including an absorbent body 11 that absorbs excreta; a back waist part 30 located on one end of the absorbent main body 10; an abdominal waist part 40 located on the other side of the absorbent main body 10. Among these diapers 1, some may be provided with a pair of embossed lines 50, formed by embossing, on both side parts in the lateral direction of the absorbent body 11. Then, with provision of such embossed lines 50, apart of the absorbent body 11 corresponding to a crotch can be formed in a simple cup shape (which is formed such that the absorbent body 11 is folded along the embossed lines 50 and the absorbent body outer parts 16, located on the outer side with respect to the embossed lines 50, stand up), thereby being able to create a space to contain excreta.

However, in the diaper 1 according to a conventional example, since the embossed lines 50 are provided to form the absorbent body 11 in a cup shape at a crotch, a part of the absorbent body 11 corresponding to a part on the back side with respect to a crotch, i.e., buttocks, is affected by the embossed lines 50, and thereby the absorbent body outer parts 16 stand up (slip inward) also at buttocks, which causes a problem that buttocks could not be widely covered with the absorbent body 11. In such a case, an area of a part that covers buttocks in the absorbent body 11 is reduced, which may have caused excreta leakage.

Whereas, in a present embodiment, by devising forms of the embossed lines 50, it becomes possible to form a part of the absorbent body 11 corresponding to a crotch in a simple cup shape and widely cover buttocks with the absorbent body 11, while maintaining superiority in creation of a space to contain excreta.

First, the former superiority will be described. In a present embodiment, the first protrusion point 52 protruding inward in the lateral direction is located in the center or on the side of the back waist part 30 with respect to the said center, in the midsection of the diaper 1. Then, parts of the embossed lines 50 located on the side of the abdominal waist part 40 with respect to the first protrusion point 52, that is, the center lines 58 serve a function of forming the absorbent body 11 in a cup shape at a crotch. In other words, the absorbent body 11 is folded along the center lines 58 and the absorbent body outer parts 16 located on the outer side with respect to the center lines 58 stand up, and thereby the absorbent body 11 is formed in a cup shape at a crotch.

Figure 6:
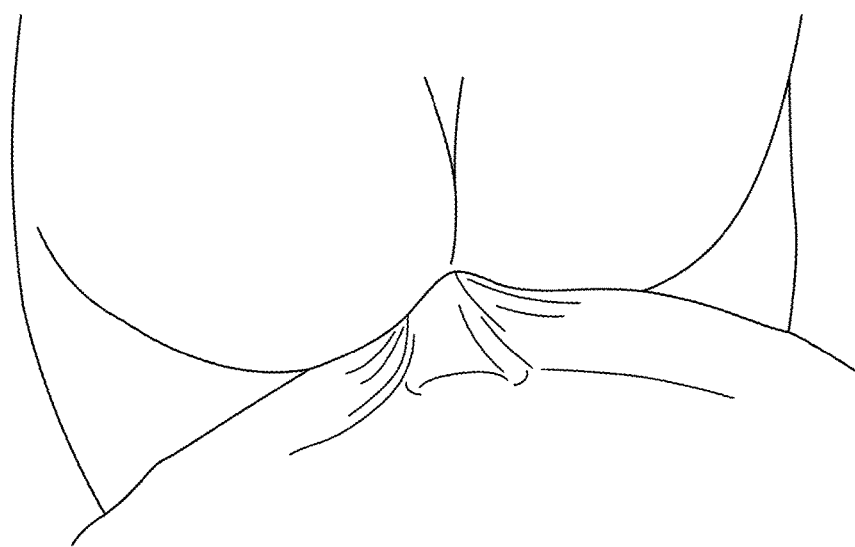
FIG. 6 is an image view illustrating a state in which an absorbent body 11 is formed in a cup shape at a crotch.
Figure 7:
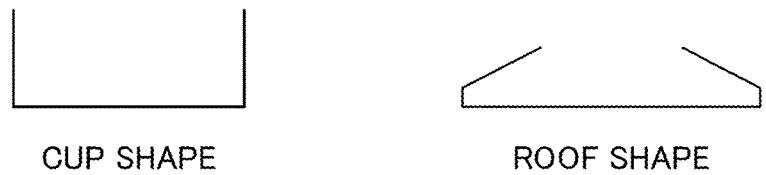
FIG. 7 is a schematic view illustrating a cup shape and a roof shape.

FIG. 6 is an image view illustrating a state in which the absorbent body 11 is formed in a cup shape at a crotch. FIG. 7 is a schematic view illustrating a cup shape and a roof shape. In FIG. 6, apart of the absorbent body 11 corresponding to a crotch is in a state where the side portions thereof slightly fall down inward resulting in a roof shape (referred to as a roof shape, for convenience' sake) as compared with the cup shape in FIG. 7. Whether to become the cup shape or the roof shape in FIG. 7 differs according to the size (large or small) of the diaper 1 with respect to the size of a human body, the degree of pressure exerted by inner thighs, and the like. In a present embodiment, the cup shape and the roof shape are described as a cup shape in a broad sense.

Then, when the absorbent body 11 is formed in the cup shape at a crotch, a space to contain excreta is created at the bottom of the cup. Thus, it becomes possible to cause skin not to touch excreta as much as possible.

Further, since the embossed lines 50 (reference numeral 58 represents center lines) are formed in the absorbent body 11, the absorbent body 11 at a crotch is formed in a simple shape. If the embossed lines 50 (reference numeral 58 represents the center lines) are not formed, wrinkles occur at random, and bumps (unevenly raised portions) and dips are formed unevenly. That is, since the embossed lines 50 (reference numeral 58 represents the center lines) are not provided, the absorbent body 11 is not settled in a certain shape, which raises the possibility of resulting in a shape visually and functionally not preferable (for example, a state where bump places are inclined to one side), depending on the cases (differs according to whether the size of the diaper 1 is large (or small) relative to the size of a human body, the degree of pressure exerted by inner thighs, and the like). Whereas, in a present embodiment, since the embossed lines 50 (reference numeral 58 represents the center lines) are formed, the absorbent body 11 is settled in a cup shape, which is a simple form, with high probability.

Further, in a present embodiment, since embossing is carried out from the skin side, the depression 50a is formed on the skin side as illustrated in FIG. 5. Thus, the absorbent body 11 is easily folded in a desired direction along the center lines 58. That is, the absorbent body 11 is easily folded, not in a mountain fold, but in a valley fold when seen from the skin side.

Next, the latter superiority will be described. In a present embodiment, the back line 56 is to be provided which is straight or curved outward and extends outward in the lateral direction from the first protrusion point 52, serving as a starting point, toward the back waist part 30 in the longitudinal direction. Thus, buttocks can be extensively covered with the absorbent body 11. That is, if the back line 56 is an inwardly curved line, an area of a part covering buttocks in the absorbent body 11 is outstandingly reduced when the absorbent body outer parts 16 stand up at buttocks, and thus such an event that excreta leakage may easily occurs. Furthermore, since the absorbent body outer parts 16 enter into the inner side, the so-called half-covered buttocks state in which the absorbent body 11 is inserted between buttocks occurs, which may result in a problem that a user feels unpleasant to the touch.

Whereas, in a present embodiment, since the back line 56 is to be a straight line or an outwardly curved line, buttocks can be extensively covered with the absorbent body 11, thereby being able to restrain occurrence of excreta leakage. Furthermore, by reducing occurrence of the half-covered buttocks state, it becomes possible to restrain a user from feeling unpleasant to the touch.

Furthermore, in a present embodiment, the back line 56 is to be an outwardly curved line. Thus, buttocks can be further extensively covered with the absorbent body 11, and still furthermore, the back line 56 can be made along a shape of buttocks (this brings such a state that the absorbent body 11 covers the entire buttocks).

Further, as will be described below, in the case where the back line 56 is an outwardly curved line, the absorbent body 11 is less easily folded along the back line 56, as compared with a case with an inwardly curved line, and thus the absorbent body outer parts 16, located on the outer side with respect to the back line 56, stand up less easily.

Figure 8:
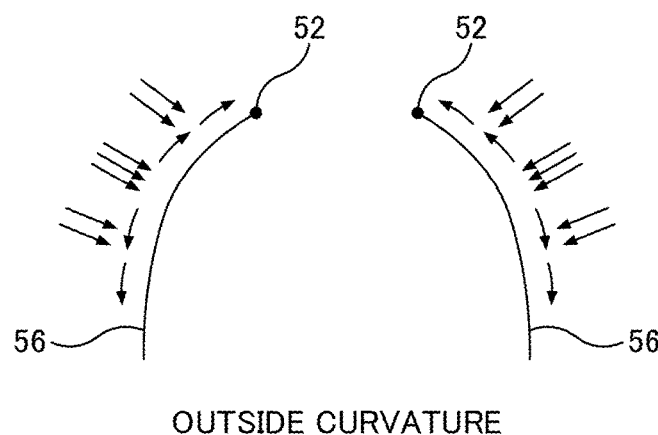
FIG. 8 is an explanatory image view to explain functional effects exerted by a back line 56 being an outwardly curved line.
Figure 8:
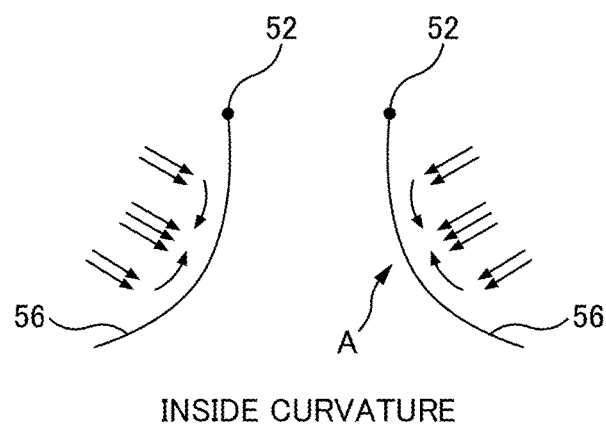

That is, in a part of the absorbent body 11 in the vicinity of the back line 56, forces in directions as indicated by arrows in FIG. 8 are generated, for example, by being pressed by inner thighs on the upper side closer to a crotch. In such a case, when the back line 56 is curved inward, the forces are overconcentrated as illustrated in a lower diagram of FIG. 8, whereas, when the back line 56 is curved outward, the forces are deconcentrated along the back line 56 as illustrated in an upper diagram of FIG. 8. Thus, in the case where the back line 56 is an outwardly curved line, the degree of standing up of the absorbent body outer parts is eased. Therefore, the absorbent body 11 is more appropriately restrained from being inserted into buttocks, thereby being able to more reliably restrain degradation of feeling to the touch. Note that FIG. 8 is an explanatory image view to explain functional effects exerted by the back line 56 being an outwardly curved line.

Further, in a present embodiment, a notch (first notch 13) is provided at a location corresponding to the position of the first protrusion point 52 in the longitudinal direction, in the side edge 12 in the lateral direction of the absorbent body 11.

In the case where the first notch 13 is provided at a location corresponding to the position of the first protrusion point 52, the absorbent body 11 is easily folded in the lengthwise direction at the position of the first protrusion point 52. That is, the absorbent body 11 is easily folded along a virtual line connecting a pair of the first protrusion points 52 (in other words, a virtual line connecting a pair of the first notches 13). Thus, a space to contain excreta can be formed more appropriately. Especially, in a present embodiment, since the position of the virtual line (first protrusion point 52, first notch 13) in the longitudinal direction corresponds to that of the anus in many cases, a space to contain excrement can be secured, with the absorbent body 11 being folded along the virtual line.

Figure 9:
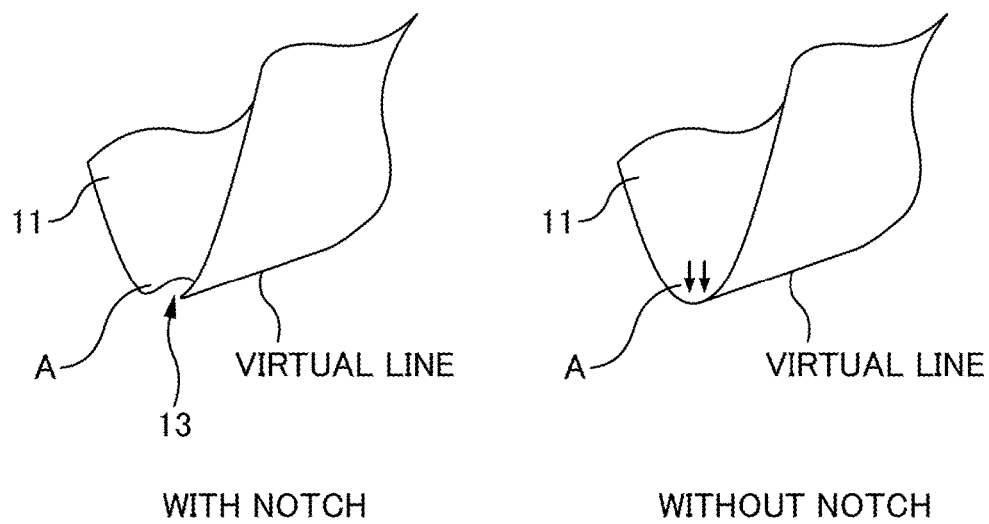
FIG. 9 is an explanatory image view to explain functional effects exerted by a first notch 13 being provided.

Further, the first notch 13 is contributed also to folding of the absorbent body 11 along the center lines 58 (standing up of the absorbent body outer parts 16 located on the outer side with respect to the center lines 58). As illustrated in a left diagram of FIG. 9, with the existence of the first notch 13, a part of the absorbent body outer part 16, adjacent to the first notch 13, indicated by a symbol A is easily folded (if the first notch 13 is not provided, as illustrated in a right diagram of FIG. 9, the forces exerted outward (see arrows) are applied to a part, which should be provided with the first notch 13, and it becomes difficult to fold at the part indicated by the symbol A). Thus, a part of the absorbent body 11 corresponding to a crotch can be formed in a simple cup shape, more appropriately. Note that FIG. 9 is an explanatory image view to explain functional effects exerted by a first notch 13 being provided.

Further, in a present embodiment, since the fold line F along the lateral direction is formed at a position corresponding to that of the first protrusion point 52 in the longitudinal direction, the absorbent body 11 is easily folded in the lengthwise direction at the position of the first protrusion point 52. That is, the absorbent body 11 is easily folded along the virtual line connecting the pair of first protrusion points 52. Thus, a space to contain excreta can be formed more appropriately.

Further, in a present embodiment, since the absorbent main body 10 is provided with elastic members (i.e., the LG rubber threads 26a and the LSG rubber threads 29) along the longitudinal direction, the absorbent body 11 is further easily folded in the lengthwise direction at the position of the first protrusion point 52 due to the elastic force of the elastic members. That is, the absorbent body 11 is further easily folded along the virtual line connecting the pair of first protrusion points 52. Thus, a space to contain excreta can be formed more appropriately.

Further, in a present embodiment, the LSG rubber threads 29 are to be located on the outer side in the lateral direction with respect to the first protrusion point 52. Thus, since the LSG rubber threads 29 contract on the outer side with respect to the first protrusion point 52, the absorbent body outer parts 16 easily stand up at a crotch. Thus, a part of the absorbent body 11 corresponding to a crotch can be more appropriately formed in a simple cup shape.

Further, the absorbent body 11 according to a present embodiment is to include: the first regions R1 (regions other than dotted parts in FIG. 2); and the second regions R2 (the dotted parts in FIG. 2) in which the absorbent polymer(s) to pulp ratio is smaller than the ratio in the first regions R1, and the embossed lines 50 are to be formed in the second regions R2.

Thus, it becomes possible to reduce the bending resistance in the parts in which the embossed lines 50 are formed, and the absorbent body outer parts 16 easily stand up at a crotch (absorbent body 11 is easily folded along the center lines 58). Thus, a part of the absorbent body 11 corresponding to a crotch can be more appropriately formed in a simple cup shape.

Further, since the first regions R1 bulge greater than the second regions R2 when the absorbent body 11 absorbs liquid (excreta), the embossed lines 50 (first regions R1) result in depressions. Thus, in such a case as well, a state in which the absorbent body 11 is folded along the center lines 58 is appropriately maintained.

Further, in a present embodiment, as illustrated in FIG. 5, raised parts 11d are to be provided to both sides of each of the embossed lines 50 in the lateral direction.

Thus, it becomes possible to avoid that the absorbent body 11 is excessively folded along the embossed lines 50 (center lines 58). That is, raised parts 11d exist on both the sides, respectively, and thus when the degree of folding of the absorbent body 11 gradually increases, both the raised parts 11d are physically interfered with each other eventually. Therefore, such interference exerts a function of stopping further folding, and thus excessively folding of the absorbent body 11 is avoided.

Further, in a present embodiment, the ending point of the back line 56 is to reach the side edge 12 in the lateral direction of the absorbent body 11. If the ending point of the back line 56 reaches a rear end 17 in the longitudinal direction of the absorbent body 11, an area of a part covering buttocks in the absorbent body 11 is outstandingly reduced. Whereas, if the ending point of the back line 56 reaches the side edge 12, as in a present embodiment, buttocks can be widely covered with the absorbent body 11.

Further, in a present embodiment, the ending point is to reach, not the back overlap part side edge 12a, but the non-overlap part side edge 12b, in the side edge 12. Thus, buttocks can be more extensively covered with the absorbent body 11.

Further, in a present embodiment, the ending point is to be located in an intermediate part, in the longitudinal direction, between the first protrusion point 52 and the lower end 30b of the back waist part 30 on the side closer to the said center.

In the case where it is provided on the side of the lower end 30b with respect to the intermediate part, an area of a part covering buttocks in the absorbent body 11 is reduced as compared with that in the case of being provided in the intermediate part, and in the case where it is provided on the side of the first protrusion point 52 with respect to the intermediate part, the back line 56 may affect the appropriate standing up of the absorbent body outer parts 16 at a crotch (the cup shape may not be securely formed). Therefore, in a present embodiment, the ending point is located in the intermediate part, and thus the cup shape can more appropriately be formed while buttocks are being more widely covered with the absorbent body 11.

Further, in a present embodiment, the ending point of the back line 56 reaches, not the side edge of the overlap part (back overlap part side edge 12a), but the non-overlap part side edge 12b, whereas, the ending point of the abdominal line 57 is to reach the side edge of the overlap part (abdominal overlap part side edge 12c).

The abdominal line 57 is not required to be formed in such a shape as to extensively cover buttocks, since it is not on the buttocks side. Thus, the ending point of the abdominal line 57 is located, not at the non-overlap part side edge 12b, but at the abdominal overlap part side edge 12c, so that a cup shape similar to the cup shape at a crotch is continued above as much as possible in an abdomen. Thus, according to a present embodiment, a part of the absorbent body 11 corresponding to an abdomen can be formed in a simple cup shape.

Further, in a present embodiment, while the back line 56 is to be an outwardly curved line, the abdominal line 57 is to be an inwardly curved line.

The abdominal line 57 is not required to be formed in such a shape as to widely cover buttocks, since it is not on the buttocks side. Thus, in order to narrow the width of the absorbent body 11 in view of allowance for freedom of leg movements, the abdominal line 57 is formed in an inwardly curved line. Thus, according to a present embodiment, it is possible to form the absorbent body 11 in such a shape that legs are easily moved.

Further, in a present embodiment, not only a notch (first notch 13) is to be provided at the position of a side edge corresponding to that of the first protrusion point 52 in the longitudinal direction, notches (second notch 14, third notch 15) are to be provided, respectively, at the positions of side edges corresponding to those of the second protrusion point 53 and the third protrusion point 54 in the longitudinal direction.

Thus, the absorbent body 11 is easily folded in the lengthwise direction, not only at the position of the first protrusion point 52 but also at the positions of the second protrusion point 53 and the third protrusion point 54. As a result, a space to contain an excretory portion can be more appropriately formed throughout the entire crotch portion.

Other Embodiments

The above embodiments are intended to facilitate the understanding of the present invention but not to limit the invention. And it is needless to say that modifications and improvements of the present invention are possible without departing from the scope of the invention, and equivalents thereof are also encompassed by the invention.

In the above embodiments, although a notch (first notch 13, second notch 14, third notch 15) is to be provided in the absorbent body 11 (absorbent core) containing pulp and absorbent polymers, a notch is not provided in a core wrap (upper core wrap 22 and lower core wrap 23) corresponding to the position of the notch. However, this is not limited thereto, a notch may be provided in not only the absorbent body 11 but also the core wrap (the absorbent body 11 and the core wrap may be integrally notched).

Further, in the above described embodiments, the diaper 1 is a so-called three-piece type and is structured with three separate components. That is, each of the absorbent main body 10, the back waist part 30, and the abdominal waist part 40 is one component. However, this is not limited thereto, and the diaper 1 may be structured with two components, or structured such that three parts are integrally provided.

REFERENCE SIGNS LIST 1 diaper, 1a waist opening, 1b leg opening,
10 absorbent main body, 10a one end section, 10b the other end section
11 absorbent body
11a back overlap part, 11b non-overlap part
11c abdominal overlap part, 11d raised part
12 side edge,
12a back overlap part side edge, 12b non-overlap part side edge,
12c abdominal overlap part side edge
13 first notch, 14 second notch, 15 third notch
16 absorbent body outer part
17 rear end
22 upper core wrap, 23 lower core wrap
24 top sheet member
25 back sheet member, 25a leak-proof sheet, 25b exterior sheet
26 side flap, 26a LG rubber threads, 26b side film
28 top part, 29 LSG rubber threads
30 back waist part, 30a both edge parts, 30b lower end
32 illustration sheet, 33 back rubber threads
40 abdominal waist part, 40a both edge parts, 40b lower end
42 illustration sheet, 43 abdominal rubber threads
50 embossed line, 50a depression, 50b compressed part
52 first protrusion point, 53 second protrusion point, 54 third protrusion point
56 back line, 57 abdominal line,
58 centerline, 58a first centerline, 58b second centerline
F fold line
LG leg gathers
LSG leg gathers
R1 first region, R2 second region

The invention claimed is:

1. A disposable diaper having a longitudinal direction and a lateral direction intersecting the longitudinal direction, the disposable diaper comprising:
an absorbent main body including an absorbent body that absorbs excreta;
a back waist part located on one end side of the absorbent main body; and
an abdominal waist part located on an other end side of the absorbent main body,
the absorbent body having both side parts, in the lateral direction, provided with a pair of embossed lines that is formed by embossing from a skin side of the absorbent body,
the embossed lines each including
a protrusion point, protruding inward in the lateral direction, located in a center of the disposable diaper or on a back-waist-part side with respect to said center, in the longitudinal direction, in a midsection of the disposable diaper, and
a back line extending outward in the lateral direction from the protrusion point, serving as a starting point, toward the back waist part in the longitudinal direction, the back line being a straight line or an outwardly curved line,
the absorbent body containing pulp and absorbent polymer,
the absorbent body including first regions, and second regions in which a ratio of absorbent polymer divided by pulp is smaller than the ratio in the first regions,
the embossed lines being provided in the second regions,
raised parts being provided to both sides of the embossed lines in the lateral direction,
the absorbent body has
side edges opposing each other in the lateral direction,
a back overlap part overlapping the back waist part, and
a back non-overlap part not overlapping the back waist part,
an ending point of the back line reaches one of the side edges of the absorbent body,
each of the back overlap part and the back non-overlap part has side edges opposing each other in the lateral direction,
each of the side edges of the absorbent body coincides with one of the side edges of the back overlap part and one of the side edges of the back non-overlap part, and
the ending point of the back line reaches one of the side edges of the back non-overlap part.

2. The disposable diaper according to claim 1, wherein the absorbent body further has
a notch at a location corresponding to a position of the protrusion point in the longitudinal direction, in each of the side edges of the absorbent body.

3. The disposable diaper according to claim 1, wherein the absorbent main body has a fold line extending along the lateral direction at a location corresponding to a position of the protrusion point in the longitudinal direction.

4. The disposable diaper according to claim 1, wherein the absorbent main body includes elastic members extending along the longitudinal direction.

5. The disposable diaper according to claim 4, wherein the elastic members are rubber threads forming leg side gathers, and
the rubber threads are located on an outer side in the lateral direction with respect to the protrusion point.

6. The disposable diaper according to claim 1, wherein the back line is the outwardly curved line.

7. The disposable diaper according to claim 1, wherein the back waist part has upper and lower ends in the longitudinal direction,
the lower end is located between the center of the disposable diaper and the upper end in the longitudinal direction, and
the ending point of the back line is located between the lower end of the back waist part and the protrusion point in the longitudinal direction.

8. The disposable diaper according to claim 1, wherein the embossed lines each further include
a protrusion point, different from the protrusion point, located on an abdominal-waist-part side with respect to the center of the disposable diaper, and
an abdominal line extending outward in the lateral direction from the second protrusion point toward the abdominal waist part in the longitudinal direction,
the second protrusion point is a starting point of the abdominal line,
an ending point of the abdominal line reaches one of the side edges of the absorbent body,
the absorbent body has
an abdominal overlap part overlapping the abdominal waist part; and
an abdominal non-overlap part not overlapping the abdominal waist part,
each of the abdominal overlap part and the abdominal non-overlap part has side edges opposing each other in the lateral direction,
each of the side edges of the absorbent body coincides with one of the side edges of the abdominal overlap part and one of the side edges of the abdominal non-overlap part.

9. The disposable diaper according to claim 8, wherein the embossed lines each further include a third protrusion point between the protrusion point and the second protrusion point in the longitudinal direction, and
the absorbent body includes notches respectively provided at locations corresponding to positions of the second protrusion point and the third protrusion point in the longitudinal direction, in the side edges of the absorbent body.

10. The disposable diaper according to claim 1, wherein the embossed lines each further include
a second protrusion point, different from the protrusion point, located on an abdominal-waist-part side with respect to the center of the disposable diaper, and
an abdominal line extending outward in the lateral direction from the second protrusion point toward the abdominal waist part in the longitudinal direction,
the second protrusion point is a starting point of the abdominal line, and
the abdominal line is an inwardly curved line.

11. The disposable diaper according to claim 1, wherein the absorbent body includes a periphery having side portions opposing each other in the lateral direction, and
the ending point of the back line reaches one of the side portions of the periphery of the absorbent body.

12. A disposable diaper having a longitudinal direction and a lateral direction intersecting the longitudinal direction, the disposable diaper comprising:
an absorbent main body including an absorbent body that absorbs excreta;
a back waist part located on one end side of the absorbent main body; and
an abdominal waist part located on an other end side of the absorbent main body,
the absorbent body having both side parts, in the lateral direction, provided with a pair of embossed lines that is formed by embossing from a skin side of the absorbent body,
the embossed lines each including
a protrusion point, protruding inward in the lateral direction, located in a center of the disposable diaper or on a back-waist-part side with respect to said center, in the longitudinal direction, in a midsection of the disposable diaper, and
a back line extending outward in the lateral direction from the protrusion point, serving as a starting point, toward the back waist part in the longitudinal direction, the back line being a straight line or an outwardly curved line,
the absorbent body containing pulp and absorbent polymer,
the absorbent body including first regions, and second regions in which a ratio of absorbent polymer divided by pulp is smaller than the ratio in the first regions,
the embossed lines being provided in the second regions, and
raised parts being provided to both sides of the embossed lines in the lateral direction,
the absorbent body has
side edges opposing each other in the lateral direction, and
a notch at a location corresponding to a position of the protrusion point in the longitudinal direction, in each of the side edges of the absorbent body.

* * * * *